United States Patent
Kodama et al.

(10) Patent No.: US 7,655,810 B2
(45) Date of Patent: Feb. 2, 2010

(54) PHOSPHINE TRANSITION METAL COMPLEX, METHOD FOR PRODUCING THE SAME, AND ANTITUMOR AGENT CONTAINING THE SAME

(75) Inventors: Hiroaki Kodama, Saga (JP); Keisuke Ohto, Saga (JP); Nobuhiko Oohara, Tokyo (JP); Kazuhiro Nakatsui, Tokyo (JP); Yoshirou Kaneda, Tokyo (JP)

(73) Assignee: Nippon Chemical Industrial Co., Ltd., Tokyo (JP)

( * ) Notice: Subject to any disclaimer, the term of this patent is extended or adjusted under 35 U.S.C. 154(b) by 50 days.

(21) Appl. No.: 12/096,316

(22) PCT Filed: Nov. 30, 2006

(86) PCT No.: PCT/JP2006/323886

§ 371 (c)(1),
(2), (4) Date: Jun. 5, 2008

(87) PCT Pub. No.: WO2007/066557

PCT Pub. Date: Jun. 14, 2007

(65) Prior Publication Data

US 2009/0156850 A1     Jun. 18, 2009

(30) Foreign Application Priority Data

Dec. 6, 2005     (JP) ............................ 2005-352466

(51) Int. Cl.
*A61K 31/28* (2006.01)
*C07F 15/00* (2006.01)

(52) U.S. Cl. ................. 556/18; 556/20; 514/492; 514/495; 514/499; 568/12

(58) Field of Classification Search .............. 556/18, 556/20; 568/12; 514/492, 495, 499
See application file for complete search history.

(56) References Cited

U.S. PATENT DOCUMENTS 6,946,569 B2    9/2005   Zhang

FOREIGN PATENT DOCUMENTS

JP          2002-523419 A      7/2002

OTHER PUBLICATIONS

Berners-Price et al., Journal of Medicinal Chemistry, vol. 33, No. 5, pp. 1386-1392 (1990).*
Berner-Price, Susan J. et al. "Cytotoxicity and Antitumor Activity of Some TetrahedralBis (diphosphino) gold (I) Chelates", Journal of Medicinal Chemistry, 1990, vol. 33, No. 5, p. 1386-1392; p. 1387, Table I complex 15; pp. 1391 to 1392; Production Method experimental Section (15).
Marinetti, A. et al. Chiral 1, 2-bis (phosphetano)ethanes, Journal of Organometallic Chemistry, 2001, vol. 624, No. 1-2, p. 162-166; p. 164; Fig. 1.
International Search Report of PCT/JP2006/323886, date of mailing Feb. 6, 2007.

* cited by examiner

*Primary Examiner*—Porfirio Nazario Gonzalez
(74) *Attorney, Agent, or Firm*—Westerman, Hattori, Daniels & Adrian, LLP

(57) ABSTRACT

A phosphine transition metal complex is expressed by general formula (1):

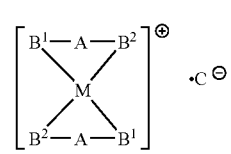

(1)

wherein A represents a groups selected from among alkylene, phenylene, and cis-vinylene; M represents an atom selected from the group consisting of gold, silver, copper, and platinum; $B^1$ and $B^2$ each represent a substituted or unsubstituted heterocyclic group containing a trivalent phosphorus atom forming a covalent bond with A and coordinating with M; and C represents an anionic atom.

7 Claims, No Drawings

PHOSPHINE TRANSITION METAL COMPLEX, METHOD FOR PRODUCING THE SAME, AND ANTITUMOR AGENT CONTAINING THE SAME

BACKGROUND OF THE INVENTION

1. Field of the Invention

The present invention relates to a new phosphine transition metal complex, a method for producing the same, and an antitumor agent containing the same.

2. Description of the Related Art

Platinum complexes such as cisplatin (cis-dichlorodiamine platinum (II)), carboplatin (cis-1,1-cyclobutanedicarboxylate diamine platinum (II)), and nedaplatin (cis-O,O'-glycolate diamine platinum (II)) have high antitumor activity and are used as principal antitumor agents.

PCT Japanese Translation Patent Publication No. 10-509957 discloses phosphine transition metal complexes expressed by general formula (4):

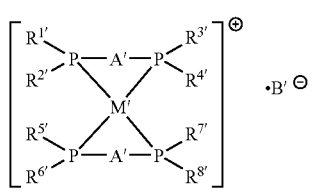

(4)

wherein $R^{1\prime}$ to $R^{8\prime}$ may be the same or different and each represent phenyl, substituted phenyl, or pyridyl; A' represents linear alkylene or cis-vinylene; M' represents gold, silver, or copper; and B' represents an anion species. Japanese Unexamined Patent Application Publication No. 61-10594 also discloses phosphine transition metal complexes expressed by the same general formula (4), wherein $R^{1\prime}$ to $R^{8\prime}$ all represent the same phenyl, substituted phenyl, or ethyl, or $R^{1\prime}$, $R^{2\prime}$, $R^{7\prime}$ and $R^{8\prime}$ represent phenyl while $R^{3\prime}$ to $R^{6\prime}$ represent ethyl; A represents a linear alkylene or cis-vinylene; M' represents gold, silver, or copper; and B' represents an anionic species. It is known that these phosphine transition metal complexes have antitumor activity comparable to that of cisplatin.

In general, however, the antitumor activity and antitumor spectrum of a compound heavily depend on the chemical structure, and a small change in the structure results in a large difference in characteristics. In addition, the efficacy of an antitumor agent varies depending on the person. For example, even taxol, which is considered to be the most effective antitumor agent, exhibits an effectiveness of at most about 30%. It is desired that a variety of new antitumor agents having different structures are developed.

SUMMARY OF THE INVENTION

Accordingly, an object of the present invention is to provide a new phosphine transition metal complex having superior antitumor activity, a method for producing the same, and an antitumor agent containing the same.

The inventors of the present invention have conducted intensive research for a new phosphine transition metal complex having antitumor activity and found that phosphine transition metal complexes having a specific structure exhibit superior antitumor activity.

According to an aspect of the invention, a phosphine transition metal complex expressed by general formula (1) is provided:

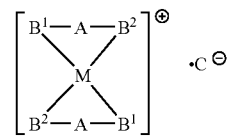

(1)

wherein A represents a group selected from among alkylene, phenylene, and cis-vinylene; M represents an atom selected from the group consisting of gold, silver, copper, and platinum; $B^1$ and $B^2$ each represent a substituted or unsubstituted heterocyclic group containing a trivalent phosphorus atom forming a covalent bond with A and coordinating with M; and C represents an anionic atom.

Preferably, the phosphine transition metal complex is specifically expressed by general formula (2):

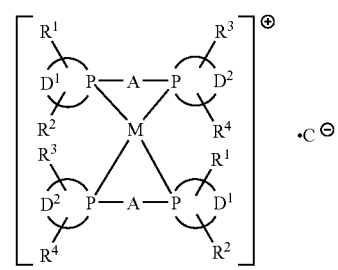

(2)

wherein A, M, and C are the same as specified above; $D^1$ and $D^2$ each represent an alkylene group; and $R^1$, $R^2$, $R^3$, and $R^4$ each represent a group selected from the group consisting of hydrogen, alkyl, hydroxyalkyl, phenyl, benzyl, carbonyl, amino, and hydroxyl.

Preferably, $D^1$ and $D^2$ each represent a tetramethylene group and $R^1$, $R^2$, $R^3$, and $R^4$ each represent a lower alkyl group.

Preferably, M is gold.

Preferably, the phosphine transition metal complex is one selected from the group consisting of bis(1,2-bis(2,5-dimethylphosphorano)ethane)gold (I) chloride, bis(1,2-bis(2,5-diethylphosphorano)ethane)gold (I) chloride, bis(1,2-bis(2,5-diisopropylphosphorano)ethane)gold (I) chloride, bis(1,2-bis(2,5-(dimethylphosphorano)benzene)) gold (I) chloride, bis(1,2-bis(2,5-(diethylphosphorano)benzene))gold (I) chloride, bis(1,2-bis(2,5-(diisopropylphosphorano)benzene))gold (I) chloride, bis(1,2-bis(2,5-(dimethyl)-3,4-(dihydroxy)phosphorano)benzene))gold (I) chloride, and bis(1,2-bis(2,5-(dimethyl)-3,4-(dibenzyloxy)phosphorano)benzene))gold (I) chloride.

The phosphine transition metal complex may have optical activity.

According to another aspect of the invention, a method for producing a phosphine transition metal complex expressed by general formula (1):

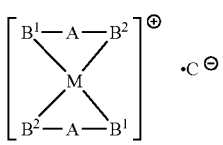

(1)

In the formula, A represents a groups selected from among alkylene, phenylene, and cis-vinylene; M represents an atom selected from the group consisting of gold, silver, copper, and platinum; $B^1$ and $B^2$ each represent a substituted or unsubstituted heterocyclic group containing a trivalent phosphorus atom forming a covalent bond with A and coordinating with M; and C represents an anionic atom. The method includes the step of allowing a salt containing a metal selected from the group consisting of gold, silver, copper, and platinum with a bisphosphine derivative expressed by general formula (3):

$$B^1\text{-}A\text{-}B^2 \qquad (3)$$

In the formula, A, $B^1$, and $B^2$ are the same as specified in general formula (1).

According to another aspect of the invention, an antitumor agent containing a phosphine transition metal complex expressed by general formula (1):

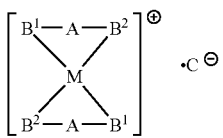

(1)

In the formula, A represents a group selected from among alkylene, phenylene, and cis-vinylene; M represents an atom selected from the group consisting of gold, silver, copper, and platinum; and $B^1$ and $B^2$ each represent a substituted or unsubstituted heterocyclic group containing a trivalent phosphorus atom forming a covalent bond with A and coordinating with M; and C represents an anionic atom.

The phosphine transition metal complex of the present invention has superior antitumor activity and is thus useful to prevent a various types of cancer and useful as an antitumor agent. The phosphine transition metal complex has low side effects and thus can be used safely. The method of the invention can produce the phosphine transition metal complex in an industrially advantageous manner.

DESCRIPTION OF THE PREFERRED EMBODIMENTS

Preferred embodiments of the invention will now be described.

The phosphine transition metal complex according to an embodiment of the invention is expressed by general formula (1):

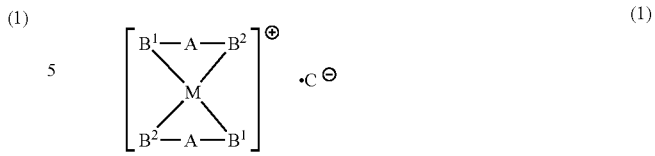

In the formula, A represents a group selected from among alkylene, phenylene, and cis-vinylene; M represents an atom selected from the group consisting of gold, silver, copper, and platinum; $B^1$ and $B^2$ each represent a substituted or unsubstituted heterocyclic group containing a trivalent phosphorus atom forming a covalent bond with A and coordinating with M; and C represents an anionic atom.

The group designated by A in general formula (1) may be alkylene, phenylene, or cis-vinylene. Exemplary alkylene groups include methylene, ethylene, trimethylene, tetramethylene, pentamethylene, propylene, and ethylethylene. These alkylene groups may be linear or branched. Among these preferred are ethylene and phenylene.

M may be gold, silver, copper, or platinum, and preferably gold.

$B^1$ and $B^2$ each represents a heterocyclic group containing a trivalent phosphorus atom forming a covalent bond with A and coordinating with M. The heterocyclic group may or may not have a substituent. Examples of such a heterocyclic group include phosphetanyl, phospholanyl, phosphinanyl, phosphepanyl, and phosphokanyl. Substituents of those groups include functional groups such as carbonyl, amino, and hydroxyl; alkyl groups, such as methyl, ethyl, propyl, isopropyl, butyl, sec-butyl, and tert-butyl; hydroxyalkyl groups, such as hydroxymethyl and hydroxyethyl; and benzyl.

$B^1$ and $B^2$, whose conformations can vary depending on the position and the type of the substituent, may be the same or different in conformation. If, for example, $B^1$ has at least one asymmetry point and its conformation is expressed by, for example, R or RR, the conformation of $B^2$ may be expressed by R or RR as with $B^1$, or reversely by S or SS. If the phosphine transition metal complex is optically active, however, it is particularly preferable that $B^1$ and $B^2$ have the same conformation.

C represents an anionic species. Examples of C include halogens, such as chlorine, bromine, and iodine, and anionic forms, such as boron fluoride, hexafluorophosphate, and perchlorate. Preferably, C is a halogen atom, such as chlorine, bromine, or iodine.

Preferably, the phosphine transition metal complex is expressed by general formula (2):

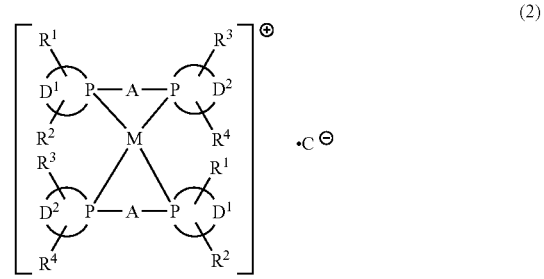

(2)

In the formula, A, M, and C are the same as specified above. $D^1$ and $D^2$ each represent an alkylene group. $R^1$, $R^2$, $R^3$, and $R^4$ each represent a group selected from the group consisting of hydrogen, alkyl, hydroxyalkyl, phenyl, benzyl, carbonyl, amino, and hydroxyl.

In general formula (2), $D^1$ and $D^2$ may be the same or different alkylene groups. Exemplary alkylene groups include linear alkylene groups having a carbon number in the range of 2 to 10, preferably 3 to 6, such as ethylene, trimethylene, tetramethylene, and pentamethylene. Among those preferred is tetramethylene.

$R^1$, $R^2$, $R^3$, and $R^4$ may be the same or different for each other, and each represent hydrogen, alkyl, hydroxyalkyl, phenyl, benzyl, carbonyl, amino, or hydroxyl. Exemplary alkyl groups include linear or brunched alkyl groups having a carbon number in the range of 1 to 10, preferably 1 to 5, such as methyl, ethyl, propyl, isopropyl, butyl, sec-butyl, tert-butyl, pentyl, isopentyl, and neopentyl. Exemplary hydroxyalkyl groups include hydroxymethyl and hydroxyethyl. $R^1$, $R^2$, $R^3$, and $R^4$ are particularly preferably methyl.

Preferred phosphine transition metal complexes include bis(1,2-bis(2,5-dimethylphosphorano)ethane)gold (I) chloride, bis(1,2-bis(2,5-diethylphosphorano)ethane)gold (I) chloride, bis(1,2-bis(2,5-diisopropylphosphorano)ethane) gold (I) chloride, bis(1,2-bis(2,5-(dimethylphosphorano) benzene))gold (I) chloride, bis(1,2-bis(2,5-(diethylphosphorano)benzene))gold (I) chloride, bis(1,2-bis(2,5-(diisopropylphosphorano)benzene))gold (I) chloride, bis(1, 2-bis(2,5-(dimethyl)-3,4-(dihydroxy)phosphorano) benzene))gold (I) chloride, and bis(1,2-bis(2,5-(dimethyl)-3, 4-(dibenzyloxy)phosphorano)benzene))gold (I) chloride.

The phosphine transition metal complex may have optical activity. Preferably, the optically active form may be (S, S)-, (R, R)-, or meso-form expressed by general formulas (5) to (10):

(5)

(6)

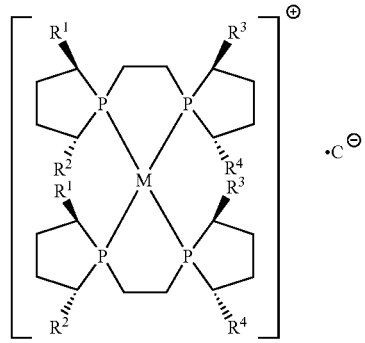

(7)

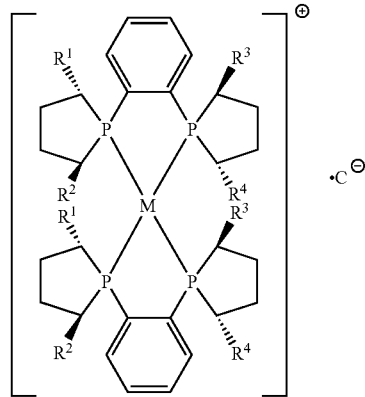

(8)

(9)

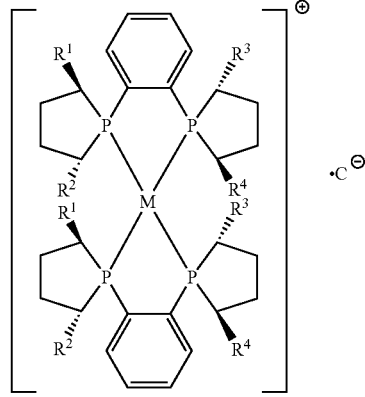

(10)

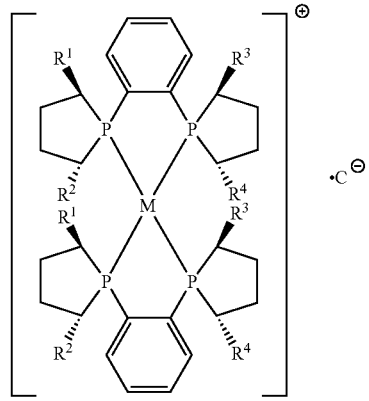

In the formulas, M, $R^1$, $R^2$, $R^3$, $R^4$, and C are as specified above.

A method for producing the phosphine transition metal complex according to an embodiment of the invention will now be described. The phosphine transition metal complex can be produced by allowing a salt containing a metal selected from the group consisting of gold, silver, copper, and platinum with a bisphosphine derivative expressed by general formula (3):

where A, $B^1$, and $B^2$ are as specified above.

The raw material, that is, the bisphosphine derivative expressed by general formula (3), is a known compound that can be prepared by a known process. For example, the bisphosphine derivative can be prepared by a reaction expressed by reaction formula (I):

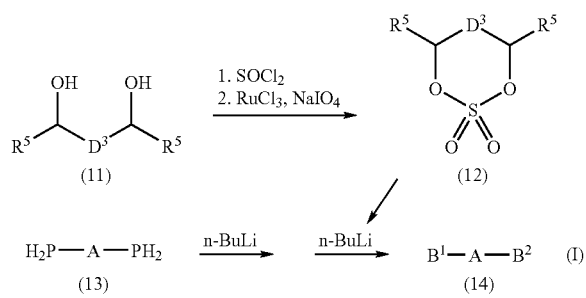

where A, $B^1$, and $B^2$ are as specified above; $R^5$ represents an lower alkyl group, such as methyl, ethyl, and isopropyl; $D^3$ represents an alkylene group having a carbon number in the range of 1 to 5.

For this reaction, first, diol (compound (11)) may be allowed to react with thionyl chloride to produce a diol cyclosulfite. Subsequently, the diol cyclosulfite is allowed to react with $NaIO_4$ in the presence of a catalytic amount of $RuCl_3$ to yield a diol cyclosulfate (compound (12)). Then, a bisphosphine compound (compound (13)) is allowed to react with a strong base, such as n-butyl lithium. The diol cyclosulfate (compound (12)) is added to the reaction system, and further a strong base, such as n-butyl lithium, is added to produce a desired bisphosphine derivative (compound (14)) (see, for example, PCT Japanese Translation Patent Application Publication No. 6-508848; J. Am. Chem. Soc., Vol. 115, No. 22, 1993, p. 10125; Tetrahedron Lett., Vol. 38, 1997, p. 2947; Synlett, 1997, p. 1975; J. Org., Chem., Vol. 63, 1998, p. 8031; Chem. Euro. J., Vol. 5, 1999, p. 1160, Eur. J. Org. Chem., 2000, p. 4615; J. Org. Chem., Vol. 65, 2000, p. 600; J. Org. Chem., Vol. 65, 2000, p. 3489; etc.)

In order to produce an optically active phosphine transition metal complex expressed by general formula (1), an optically active bisphosphine derivative expressed by general formula (3) can be allowed to react with a salt of a transition metal selected from the group consisting of gold, copper, platinum, and silver. In order to produce an optically active bisphosphine derivative expressed by general formula (3), an optically active 1,4-diol can be used as the starting material 1,4-diol (compound (11)) in reaction formula (I).

The salt of gold, silver, copper, or platinum as the other starting material may be a halide, a nitrate, a perchlorate, a tetrafluoroborate, or a hexafluorophosphate.

Preferred gold salts include chloroauric acid, gold (I) chloride, and tetrabutylammonium chloride-gold (I) chloride (see "Jikken KagakuKoza 21 (Courses in Experimental Chemistry), 5th Ed.", edited by The Chemical Society of Japan, published by Maruzen Co., Ltd., published on March 30, Heisei 16 (2004), p.p. 366-380; and Aust. J. Chem., 1997, 50, p.p. 775-778). Preferred copper salts include copper (I) chloride, copper (I) bromide, and copper (I) iodide (see "Jikken KagakuKoza 21 (Courses in Experimental Chemistry), 5th Ed." edited by The Chemical Society of Japan, published by Maruzen Co., Ltd., published on March 30, Heisei 16 (2004), p.p. 349-361). Preferred platinum salts include platinum (II) chloride, and sodium tetrachloroplatinate (II), potassium tetrachloroplatinate (II) (Courses in Experimental Chemistry), 5th Ed." edited by The Chemical Society of Japan, published by Maruzen Co., Ltd., published on March 30, Heisei 16 (2004), p.p. 327-348). Preferred silver salts include silver (I) chloride, silver (I) bromide, and silver (I) iodide (Courses in Experimental Chemistry), 5th Ed." edited by The Chemical Society of Japan, published by Maruzen Co., Ltd., published on March 30, Heisei 16 (2004), p.p. 361-366). These metal salts may be anhydrides or hydrates.

In general, the reaction of the bisphosphine derivative expressed by general formula (3) with the metal salt is performed in a proportion of 1 to 5 times by mole, preferably 1.3 to 2.2 times by mole, relative to the metal salt at a temperature of −20 to 60° C., preferably 0 to 25° C., for 0.5 to 48 hours, preferably 1 to 3 hours, generally in a solvent, such as acetone, acetonitrile, methanol, or ethanol. The reaction product is purified by a conventional method, if necessary.

The phosphine transition metal complex expressed by general formula (1) can first be synthesized in a form whose anionic atom designated by C is an halogen, and then the anionic atom C is replaced with a desired anion by a reaction with an appropriate inorganic acid, organic acid, or an alkali metal salt in a solvent (see Japanese Examined Patent Application Publication No. 10-147590 and Japanese Unexamined Patent Application Publication Nos. 10-114782 and 61-10594).

The resulting phosphine transition metal complex exhibits superior antitumor activity as will be described later and can be used as an antitumor agent.

The antitumor agent of the invention contains at least one phosphine transition metal complex expressed by general formula (1), which may have optical activity.

The type of cancer for which the antitumor agent of the present invention can be used is not particularly limited. Examples of the cancer include malignant melanoma, malignant lymphoma, gastrointestinal cancer, lung cancer, esophageal cancer, gastric cancer, colon cancer, rectal cancer, colonic cancer, ureter tumors, gallbladder cancer, cholangiocarcinoma, biliary tract cancer, breast cancer, hepatoma, pancreas cancer, orchioncus, maxillary cancer, tongue cancer, lip cancer, oral cancer, pharyngeal cancer, laryngeal cancer, ovarian cancer, uterine cancer, prostate cancer, thyroid cancer, brain tumors, Kaposi's sarcoma, angioma, leukemia, polycythemia vera, neuroblastoma, retinoblastoma, myeloma, bladder tumor, sarcoma, osteosarcoma, myosarcoma, skin cancer, basal cell carcinoma, skin appendage carcinoma, metastatic skin cancer, and cutaneous melanoma. The antitumor agent may be used for benign tumors as well as malignant tumors. The antitumor agent may be used to inhibit cancer metastasis, and is particularly useful as a cancer metastasis suppressor used after surgery.

The antitumor agent can be administered to humans and animals in various ways. For example, the antitumor agent may be orally administered, or parenterally administered by injections, such as intravenous injection, intramuscular injection, or hypodermic or intradermal injection, intrarectal administration, or transmucosal administration. Exemplary forms of the antitumor agent for oral administration include tablets, pills, granules, powders, capsules, liquids, suspensions, emulsions, and syrups. Exemplary forms of pharmaceutical compositions for parenteral administration include injections, drops, nasal drops, sprays, inhalants, suppository, and endermic preparations such as ointments, creams, powdery liniments, liquid liniments, and patches. Furthermore, the antitumor agent may be a long-acting preparation such as an implantable pellet or another form prepared by a known process. The way of administration and the form of the agent are appropriately selected by a doctor according to, for example, the age, sex, constitutional predisposition, and symptoms of the patient, and the timing of treatment.

In order to prepare the antitumor agent as a solid product in form of, for example, tablets, pills, powders, or granules, the phosphine transition metal complex may be mixed with an appropriate additive according to a conventional method. Examples of the additive include excipients, such as lactose, sucrose, D-mannitol, corn starch, synthetic or natural gum, and crystalline cellulose; binders, such as starch, hydroxypropyl cellulose, hydroxypropylmethyl cellulose, gum arabic, gelatin, and polyvinylpyrrolidone; disintegrants, such as carboxymethylcellulose calcium, carboxymethylcellulose sodium, starch, corn starch, and sodium alginate; lubricants, such as talc, magnesium stearate, and sodium stearate; fillers, such as calcium carbonate, sodium carbonate, calcium phosphate, and sodium phosphate; and diluents. Such a solid product may be coated with sugar, gelatin, enteric coating, or a film using a coating agent, such as hydroxypropylmethyl cellulose, saccharose, polyethylene glycol, or titanium oxide.

In order to prepare the antitumor agent as a liquid product in a form of, for example, injection, eye drops, nasal drops, inhalant, spray, lotion, syrup, solution, suspension, or emulsion, the phosphine transition metal complex is dissolved in an appropriate solvent. Examples of the solvent include purified water; buffer solutions, such as phosphate buffer solutions; physiological salt solutions, such as physiological saline, Ringer's solution, and Locke's solution; vegetable oils, such as cacao butter, sesame oil, and olive oil; and organic solvents, such as mineral oil, higher alcohols, higher fatty acids, and ethanol. Additives may be added to the resulting solution as needed. Examples of the additive include emulsifiers, such as cholesterol; suspending agents, such as gum Arabic; dispersing agents; wetting agents; surfactants, such as polyoxyethylene hydrogenated castor oil and polyethylene glycol; solubilizers, such as sodium phosphate; stabilizers, such as sugar, sugar alcohols, and albumin; preservatives, such as paraben; isotonizing agents, such as sodium chloride, glucose, and glycerol; buffers; soothing agents; adsorption inhibitors; moisturizing agents; antioxidants; colorants; sweeteners; flavor; and aromatic substances. Thus, the antitumor agent can be prepared in a form of sterile aqueous solution, nonaqueous solution, suspension, ribosome, or an emulsion. Preferably, the injection has a physiological pH, and preferably a pH in the range of 6 to 8.

In order to prepare the antitumor agent as a semi-solid product in form of, for example, lotion, cream, or ointment, the phosphine transition metal complex may be appropriately mixed with fat, fatty oil, lanolin, Vaseline, paraffin, wax, plaster, resin, plastic, glycol, a higher alcohol, glycerol, water, an emulsifier, a suspending agent, or the like.

The content of the phosphine transition metal complex in the antitumor agent varies depending on the dosage form, severity, prescribed dose, and the like. In general, the content is 0.001% to 80% by weight, and preferably 0.1% to 50% by weight relative to the total weight of the antitumor agent.

The dose of the antitumor agent is appropriately determined by the doctor according to, for example, the age, sex, body weight, and symptoms of the patient, and the administration route. In general, the amount of the agent to be administrated in terms of active constituents is about 1 µg/kg to 1,000 mg/kg per adult per day, and preferably about 10 µg/kg to 10 mg/kg per adult per day. The amount of the agent may be administrated at one time or in two or more doses (for example, about 2 to 4 times) in a day.

The antitumor agent may be used in combination with known chemotherapy, surgical treatment, radiation therapy, thermotherapy, immunotherapy, or the like.

EXAMPLES

The present invention will be further described in detail with reference to Examples below, but is not limited to the Examples.

Example 1

Bis((+)-1,2-bis((2R,5R)-2,5-dimethylphosphorano) ethane)gold (I) Chloride

Under nitrogen gas flow, 436 mg (1.69 mmol) of (+)-1,2-bis((2R,5R)-2,5-dimethylphosphorano)ethane (produced by Strem) was weighed into a well-dried two-neck flask, and 25 mL of degassed chloroform was added into the flask to dissolve the material. Then, 430 mg (0.84 mmol) of tetrabutylammonium dichloroaurate (tetrabutylammonium gold (I) dichloride) was added at one time, and the mixture was subjected to a reaction at room temperature (25° C.) for 3 hours with stirring. The reaction mixture was placed in a 50 mL separatory funnel and washed with 5 mL of 1 N hydrochloric acid aqueous solution, 10 mL of pure water three times, and 10 mL of saturated sodium chloride solution in that order, followed by dehydration with anhydrous sodium sulfate. The solvent was removed with an evaporator to yield 590 mg of white powder of the target compound. The yield was 94%.

Identification Data $^1$H NMR (CDCl$_3$); δ=1.0-1.3 (m, 24H), 1.2-1.4 (m, 4H), 1.3-1.5 (m, 4H), 1.5-1.7 (m, 4H), 1.9-2.1 (m, 8H), 2.1-2.3 (m, 8H), 2.2-2.4 (m, 4H)

$^{13}$C NMR; δ=13.78 (s), 21.3 (m), 25.1 (m), 34.1, 34.7, 36.5 (m), 36.9 (m) $^{31}$P NMR (1H decoupled, CDCl$_3$); δ=37.2 (s) IR (KBr); 2927, 2865, 1454, 1407, 1375 cm$^{-1}$ MS (FAB, POS); m/z 713 (M$^+$−Cl$^-$)

Example 2

Bis((−)-1,2-bis((2S,5S)-2,5-dimethylphosphorano) ethane)gold (I) Chloride

Under nitrogen gas flow, 423 mg (1.64 mmol) of (−)-1,2-bis((2S,5S)-2,5-dimethylphosphorano)ethane (produced by Strem) was weighed into a well-dried two-neck flask, and 25 mL of degassed chloroform was added into the flask to dissolve the material. Then, 418 mg (0.82 mmol) of tetrabutylammonium dichloroaurate (tetrabutylammonium gold (I) dichloride) was added at one time, and the mixture was subjected to a reaction at room temperature (25° C.) for 3 hours with stirring. The reaction mixture was placed in a 50 mL separatory funnel and washed with 5 mL of 1 N hydrochloric acid aqueous solution, 10 mL of pure water three times, and 10 mL of saturated sodium chloride solution in that order, followed by dehydration with anhydrous sodium sulfate. The solvent was removed with an evaporator to yield 566 mg of white powder of the target compound. The yield was 94%.

Identification Data $^1$H NMR (CDCl$_3$); δ=1.0-1.3 (m, 24H), 1.2-1.4 (m, 4H), 1.3-1.5 (m, 4H), 1.5-1.7 (m, 4H), 1.9-2.1 (m, 8H), 2.1-2.3 (m, 8H), 2.2-2.4 (m, 4H) $^{13}$C NMR; δ=13.78 (s), 21.3 (m), 25.1 (m), 34.1, 34.7, 36.5 (m), 36.9 (m) $^{31}$P NMR (1H decoupled, CDCl$_3$); δ=37.2 (s) IR (KBr); 2927, 2865, 1454, 1407, 1375 cm$^{-1}$ MS (FAB, POS); m/z 713 (M$^+$–Cl$^-$)

Example 3

Bis(1,2-bis((2S,5S)-2,5-(dimethylphosphorano)benzene))gold (I) Chloride

A solution of 0.50 g (1.60 mmol) of 1,2-bis((2S,5S)-2,5-(dimethylphosphorano)benzene (produced by Strem) in degassed chloroform was placed in a 50 mL nitrogen-purged two-neck flask. Further, 0.42 g (0.80 mmol) of tetrabutylammonium dichloroaurate (tetrabutylammonium gold dichloride) was added and stirred at room temperature (25° C.) for 4 hours. The resulting solution was desiccated and recrystallized with methanol-diethyl ether. The resulting light yellow needle crystals were washed and dried under reduced pressure to yield 0.64 g of the target compound (yield: 93%).

Identification Data $^1$H NMR (300.4 MHz, CDCl$_3$); δ=0.74-0.81 (m, 12H), 1.16-1.25 (m, 12H), 1.52-1.63 (m, 4H), 1.74-1.88 (m, 4H), 2.21-2.34 (m, 8H), 2.54-2.68 (m, 8H), 7.58-7.62 (m, 4H), 7.71-7.74 (m, 4H) $^{13}$C NMR (75.5 MHz, CDCl$_3$); δ=14.4 (s), 21.3 (m), 35.7 (s), 35.9 (s), 37.5 (m), 40.3 (m), 130.6 (S), 133.2 (m), 142.2 (S) $^{31}$P NMR (121.5 MHz, CDCl$_3$) δ= 38.9 (s) MS (FAB, POS); m/z 809 (M$^+$–Cl$^-$)

Example 4

Bis(1,2-bis((2R,5R)-2,5-(dimethylphosphorano)benzene))gold (I) Chloride

A solution of 0.50 g (1.60 mmol) of 1,2-bis((2R,5R)-2,5-(dimethylphosphorano)benzene (produced by Strem) in degassed chloroform was placed in a 50 mL nitrogen-purged two-neck flask. Further, 0.42 g (0.80 mmol) of tetrabutylammonium dichloroaurate (tetrabutylammonium gold dichloride) was added and stirred at room temperature (25° C.) for 4 hours. The resulting solution was desiccated and recrystallized with methanol-diethyl ether. The resulting light yellow needle crystals were washed and dried under reduced pressure to yield 0.61 g of the target compound (yield: 89%).

Identification Data

Ms (FAB, POS); m/z 809 (M$^+$–Cl$^-$)

The products prepared in Examples 1 to 4 had structures expressed by general formula (15) below and shown in Table 1.

TABLE 1

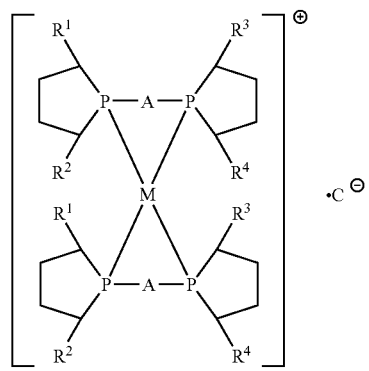

(15)

General formula (15)

| | Optically active form | R$^1$ to R$^4$ | A | M | B |
| --- | --- | --- | --- | --- | --- |
| Example 1 | R,R | methyl | ethylene | Au | Cl |
| Example 2 | S,S | methyl | ethylene | Au | Cl |
| Example 3 | S,S | methyl | phenylene | Au | Cl |
| Example 4 | R,R | methyl | phenylene | Au | Cl |

Example 5

Evaluation of Antitumor Activity

The phosphine gold complexes produced in Examples 1 to 4 were evaluated for the activities on tumor cells according to the following method. Cisplatin was also evaluated as a comparative example by the same method.

HL-60 (human acute myelocytic leukemia cells) was used as cancer cells. The cells were cultured in Rosewell Park Memorial Institute medium (RPMI 1640) supplemented with 10% fetal bovine serum, 1% antibiotic, and an antifungal agent in an atmosphere of 5% carbon dioxide in a moist incubator at 37° C.

The cells were washed with PBS. After the cell count was determined, a suspension (1×10$^5$ cells/mL) was prepared with the same medium. The suspension was seeded at a density of 50,000 cells/well in a sterile 96-well microplate.

Then, the phosphine gold complexes produced in Examples 1 to 4 and cisplatin were each completely dissolved in water or dimethyl sulfoxide. The prepared solutions were respectively added to the wells and cultured in the incubator for 24 hours.

The viable cell count was determined by a modified Mosmann method (T. Mosmann, J. Immunol. Method (1983) 65, 55-63). More specifically, a solution of a tetrazolium salt (3,[4,5-dimethylthiazole-2-yl]-2,5-diphenyltetrazolium bromide, MTT) was added to the wells. The wells were cultured for another 3 hours under the same conditions. Formazan crystals formed by the enzyme activity of mitochondria in the cells were dissolved in 0.04 mol/L HCl isopropyl alcohol solution, and the absorbance of each well was measured at 595 nm with a microplate reader (Bio-Rad 550). The background noises were canceled by subtracting the absorbance at 630 nm from the absorbance at 595 nm to obtain a viable cell count. Then, 50% inhibitory concentration (IC$_{50}$) was calculated from the viable cell count. For the calculation for IC$_{50}$, at least three measured values obtained under the same conditions were averaged. The results are shown in Table 2.

TABLE 2

| | $IC_{50}$ (μM/L) |
|---|---|
| Example 1 | 2.75 |
| Example 2 | 1.66 |
| Example 3 | 3.55 |
| Example 4 | 0.542 |
| Comparative Example 1 | 23.6 |

Table 2 clearly shows that phosphine transition metal complexes of Examples of the invention exhibited superior antitumor activity to cisplatin.

Example 6

Toxicity Test

The toxicities of the phosphine gold complex produced in Example 4 and cisplatin (Comparative Example 1) were compared by single oral administration to rats.

After female Sprauge-Dawley SPF rats (CrJ: CD (SD)) were quarantined and acclimated for about a week, healthy 8-week-old rats were selected in groups of five rats. The rats was fasted overnight before administration, and single oral doses of 20, 50, 100, and 300 mg/kg of the phosphine gold complex, and 10, 20, 50, and 100 mg/kg of cisplatin dissolved in corn oil were administrated the respective rats. The rats were observed 10 and 30 minutes and 1, 2, and 4 hours after administration, and further observed daily until the 14th day. The 50% lethal dose ($LD_{50}$) was determined from the survival rate of the rats. Table 3 shows the results.

TABLE 3

| | $LD_{50}$ |
|---|---|
| Example 4 | >300 mg/kg |
| Comparative Example 1 | 20 to 50 mg/kg |

Table 3 shows that the rats to which the phosphine gold complex of Example 4 was administrated did not die even at the 14th day, and that no specific change in general conditions, body weight, and internal organs was observed over the period of the test. These results suggest that the phosphine gold complex of the invention has low toxicity.

What is claimed is:

1. A phosphine transition metal complex expressed by general formula (2):

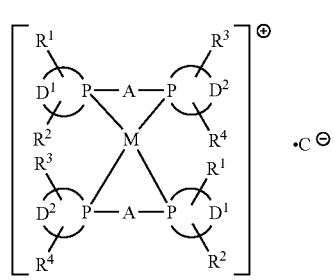

(2)

wherein A represents a group selected from the group consisting of alkylene, phenylene, and cis-vinylene;

M represents an atom selected from the group consisting of gold, silver, copper, and platinum;

C represents an anionic atom;

$D^1$ and $D^2$ each represent an alkylene group; and $R^1$, $R^2$, $R^3$, and $R^4$ each represent a group selected from the group consisting of hydrogen, alkyl, hydroxyalkyl, phenyl, benzyl, carbonyl, amino, and hydroxyl.

2. The phosphine transition metal complex according to claim 1, wherein $D^1$ and $D^2$ each represent a tetramethylene group and $R^1$, $R^2$, $R^3$, and $R^4$ each represent a lower alkyl group.

3. The phosphine transition metal complex according to claim 1, where in M is gold.

4. The phosphine transition metal complex according to claim 1, wherein the phosphine transition metal complex is one selected from the group consisting of bis(1,2-bis(2,5-dimethylphosphorano)ethane)gold (I) chloride, bis(1,2-bis(2,5-diethylphosphorano)ethane)gold (I) chloride, bis(1,2-bis(2,5-diisopropylphosphorano)ethane)gold (I) chloride, bis(1,2-bis(2,5-(dimethylphosphorano)benzene)) gold (I) chloride, bis(1,2-bis(2,5-(diethylphosphorano)benzene))gold (I) chloride, bis(1,2-bis(2,5-(diisopropylphosphorano)benzene))gold (I) chloride, bis(1,2-bis(2,5-(dimethyl)-3,4-(dihydroxy)phosphorano) benzene))gold (I) chloride, and bis(1,2-bis(2,5 -(dimethyl)-3,4-(dibenzyloxy)phosphorano)benzene))gold (I) chloride.

5. The phosphine transition metal complex according to claim 1, wherein the phosphine transition metal complex has optical activity.

6. A method for producing a phosphine transition metal complex expressed by general formula (2):

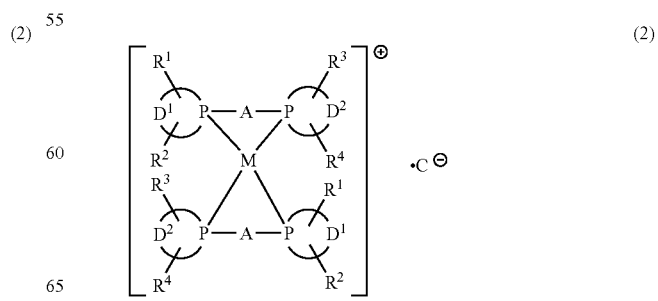

(2)

wherein A represents a group selected from the group consisting of alkylene, phenylene, and cis-vinylene;

M represents an atom selected from the group consisting of gold, silver, copper, and platinum;

$D^1$ and $D^2$ each represent an alkylene group;

$R^1$, $R^2$, $R^3$, and $R^4$ each represent a group selected from the group consisting of hydrogen, alkyl, hydroxyalkyl, phenyl, benzyl, carbonyl, amino, and hydroxyl; and C represents an anionic atom, the method comprising the step of allowing a salt containing a metal selected from the group consisting of gold, silver, copper, and platinum to react with a bisphosphine derivative expressed by the following general formula:

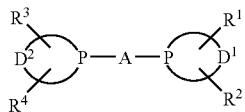

wherein A, $D^1$ and $D^2$, and $R^1$, $R^2$, $R^3$, and $R^4$, are the same as specified in general formula (2).

7. An antitumor agent containing a phosphine transition metal complex expressed by general formula (2):

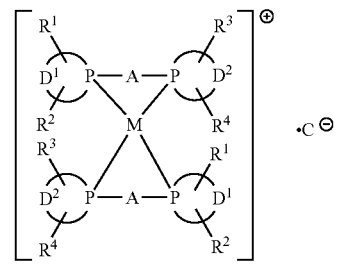

(2)

wherein A represents a group selected from the group consisting of alkylene, phenylene, and cis-vinylene;

M represents an atom selected from the group consisting of gold, silver, copper, and platinum;

$D^1$ and $D^2$ each represent an alkylene group;

$R^1$, $R^2$, $R^3$, and $R^4$ each represent a group selected from the group consisting of hydrogen, alkyl, hydroxyalkyl, phenyl, benzyl, carbonyl, amino, and hydroxyl; and C represents an anionic atom.

* * * * *